Dec. 13, 1966 M. L. MEILLAND Plant Pat. 2,693
ROSE PLANT
Filed Oct. 21, 1965
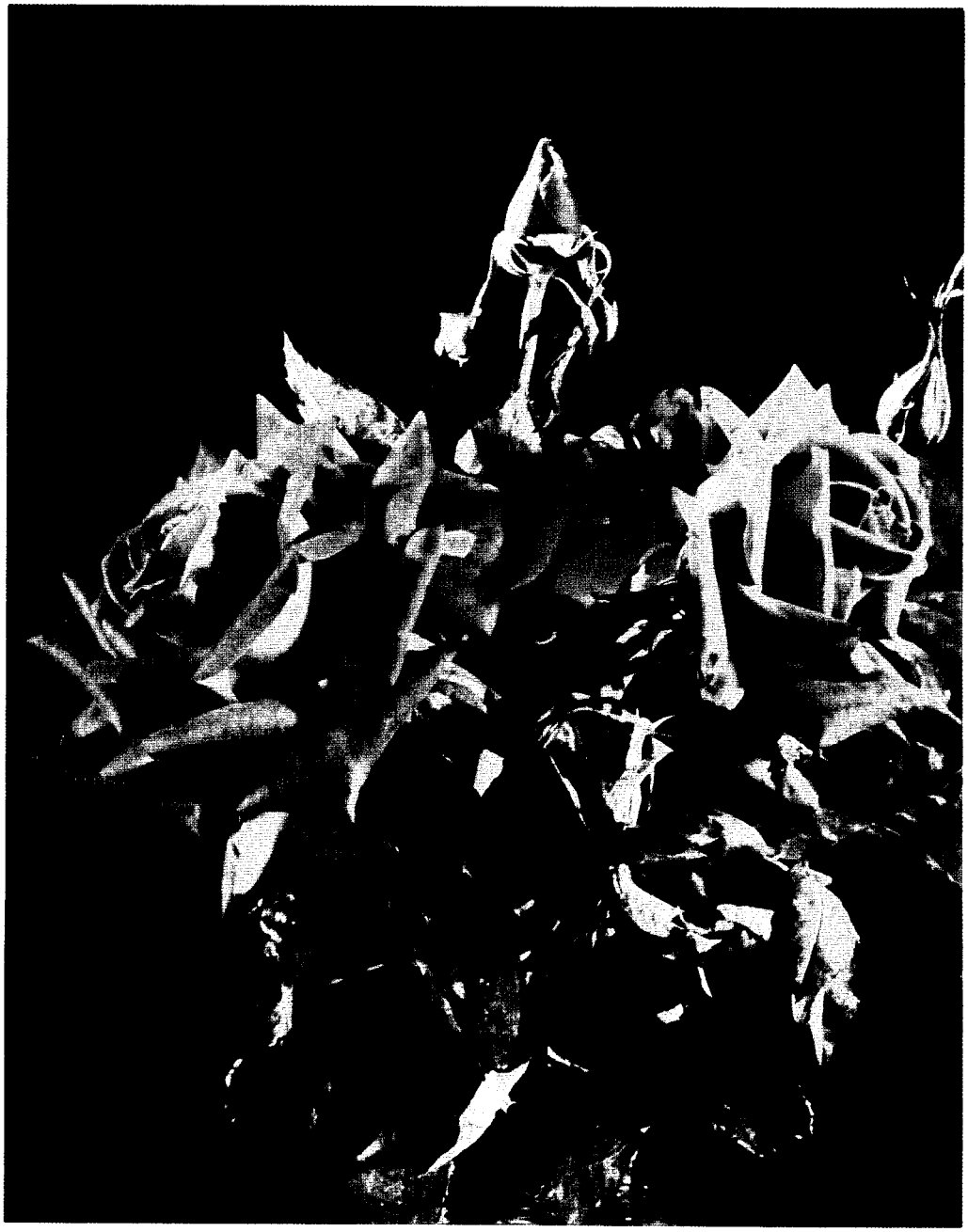
Inventor.
Marie Louise Meilland
By: Robb & Robb
Attorneys.

United States Patent Office

Plant Pat. 2,693
Patented Dec. 13, 1966

2,693
ROSE PLANT

Marie Louise Meilland, Cap d'Antibes, Alpes Maritimes, France, assignor to The Conard-Pyle Company, West Grove, Pa., a corporation of Pennsylvania Filed Oct. 21, 1965, Ser. No. 500,457
1 Claim. (Cl. Plt.—21)

The present invention relates to a new and distinct variety of rose plant of the hybrid tea class, which was originated by me by crossing the variety known as "Chrysler Imperial" (U.S. Plant Patent No. 1,167) with an unnamed and unpatented variety of unidentified parentage, the former being the seed parent and the latter being the pollen parent.

As the result of this breeding, I have produced a new and improved rose variety which is distinguished from its parents, as well as from all other varieties of which I am aware, as evidenced by the following unique combination of characteristics which are outstanding therein:

(1) A vigorous habit of growth;
(2) An attractive general appearance of the foliage;
(3) A habit of bearing flowers usually singly to a stem;
(4) An unusually large flower size; and
(5) A distinctive and attractive Tyrian Purple general color tonality of the flowers.

In comparison with its seed parent, "Chrysler Imperial," the new variety is taller in its habit of growth; its foliage is slightly lighter in color and less leathery in appearance; and its flowers are considerably larger in size and are a lighter tint of red color than in this parent variety.

As compared with its unnamed pollen parent, the new variety is considerably more vigorous in its habit of growth; its flowers are usually borne singly instead of several to a stem as in this parent; and its flowers retain their color substantially without bluing, unlike those of the parent variety.

Asexual reproduction of the new variety by budding, as performed in France, and also at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—"Chrysler Imperial."
*Pollen parent.*—An unnamed variety of unidentified parentage.
Propagation: Holds its distinguishing characteristics through succeeding propagations by budding.

*Flower*

Locality where grown and observed: West Grove, Pennsylvania, U.S.A.
Flowers borne: Usually singly to stem; on long stems of normal strength.
Quantity of bloom: Moderate, outdoors.
Continuity: Continuous.
Fragrance: Slight. Nature—tea.

Bud:
*Peduncle.*—Long; heavy; occassionally bending, but usually erect; rough; with medium number of prickles and gland-tipped hairs. Color—green.
*Before calyx breaks.*—Size—Large. Form—medium length; pointed; with a conspicuous neck; with foliaceous appendages on the surface of the bud; with stout, much-cut foliaceous parts extending beyond the tip of the bud equal to ¾ or more of its length.
*As calyx breaks.*—Color—Indian Lake, Plate 826/2.
*As first petal opens.*—Size—large. Form—medium length; ovoid. Color: Outside—Tyrian Purple, Plate 727/2, with darker shadings toward the edge of the petal; inside—near Tyrian Purple Plate 727, becoming tinted with Tyrian Purple, Plate 727/1 toward the base of the petal.
*Opening.*—Opens up well.

Bloom:
*Size (when fully open).*—Large; from 4½ inches to 6 inches.
*Petalage.*—Very double; from 50 to 55 petals; arranged regularly.
*Form.*—High-centered at first and remaining high-centered; petals being at first loosely rolled outward and remaining loosely rolled outward at maturity.

Petals:
*Texture.*—Medium thickness.
*Appearance.*—Inside—satiny. Outside—shiny.
*Shape.*—Outer—roundly obovate, with no notches. Intermediate—obovate, with no notches. Inner—very irregular, with no notches.

This description of a newly opened flower was made from a rose grown outdoors during the month of July at West, Grove, Pennsylvania, U.S.A.:

*Color.*—Outer petal: Outside surface—Tyrian Purple, Plate 727, with point of attachment Mimosa Yellow, Plate 602/2; inside surface—near Tyrian Purple, Plate 727, but slightly darker in tone, over upper half of petal, becoming progressively lighter toward base of petal, and with point of attachment Mimosa Yellow, Plate 602/1. Intermediate petal: Outside surface—Tyrian Purple, Plate 727/1, with point of attachment Mimosa Yellow, Plate 602/2; inside surface—near Tyrian Purple, Plate 727, with point of attachment Mimosa Yellow, Plate 602/1. Inner petal: Outside surface—Spiraea Red, Plate 025, sometimes streaked with China Rose, Plate 024/2 radiating from the base of the petal, with point of attachment Mimosa Yellow, Plate 602/2; inside surface—near Tyrian Purple, Plate 727, with an underlying luminescence, and with point of attachment Mimosa Yellow, Plate 602/1.

This description was made from a rose that was open for three days outdoors during the month of July at West Grove, Pennsylvania, U.S.A.:

*Color.*—Outer petal: Outside surface—Tyrian Purple, Plate 727/2, with point of attachment Mimosa Yellow, Plate 602/2; inside surface—near Tyrian Purple, Plate 727, being a somewhat darker shade toward the outer margin and becoming progressively lighter toward the base, and with point of attachment Mimosa Yellow, Plate 602/1. Inner petal: Outside surface—Tyrian Purple, Plate 727/2, with point of attachment Mimosa Yellow, Plate 602/2; inside surface—near Tyrian Purple, Plate 727, with point of attachment Mimosa Yellow, Plate 602/1.
*General color effect.*—Newly opened flower—slightly darker than Tyrian Purple, Plate 727. 3-days open—Tyrian Purple, Plate 727, with slight bluish over-tones when viewed in certain lights.

*Behavior.*—Drop off cleanly.

*Flower longevity.*—On bush in garden—4 days in July. Cut roses grown outdoors and kept at living room temperatures—3 days in July.

*Reproductive organs*

Stamens: Medium number; arranged irregularly about pistils; mixed with petaloids.

Filaments: Most with anthers; varying lengths. Color—varying from yellow at base to light orange at upper extremity.

Anthers: Open at various times; medium size; seldom an anther fused with a petaloid. Color—buff orange.

Pollen: Sparse. Color—gold.

Pistils: Many.

Styles: Uneven; medium length; medium caliper; bunched.

Stigma: Color—yellow.

Ovaries: Some protruding from receptacle.

Hips: None observed.

Sepals: Permanent; long; spear-shaped; recurved.

Seeds: None observed.

*Plant*

Foliage:

*Leaves.*—5 and occasionally 7 leaflets; normal abundance; from medium to large size; leathery.

*Leaflets.*—Shape—oval, with apex acute. Base—round. Margin—simply serrate.

*Color.*—Mature: Upper surface—Parsley Green, Plate 00962/1. Under surface—Sage Green, Plate 000861/1. Young: Upper surface—Fern Green, Plate 0862, overlaid with Oxblood Red, Plate 00823; under surface—Fern Green, Plate 0862/1 overlaid with Oxblood Red, Plate 00823.

*Rachis (the supporting stem of the compound leaf).*—Medium caliper. Upper side—grooved; hairy; edged with gland-tipped hairs. Under side—sparsely prickly.

*Stipules.*—Moderately long; medium width; with points of medium length turning out at an angle of less than 90°.

*Disease resistance.*—Comparable to that of the average variety grown under the same cultural conditions at West Grove, Pennsylvania, U.S.A.

Growth:

*Habit.*—Bushy; upright; much-branched.

*Growth.*—Moderately vigorous.

*Canes.*—Medium caliper.

*Main stems.*—Bright. Color—Spinach Green, Plate 0960/2. Prickles—many; color—brown. Hairs—several; gland-tipped; color—brown.

*Branches.*—Bright. Color—Spinach Green, Plate 0960/2. Prickles—many; color—reddish at base, becoming yellow at tip. Hairs—several; gland-tipped; color—brown.

*New shoots.*—Dull. Color—Lettuce Green, Plate 861/1. Prickles—many; color—green, tinged with reddish-brown. Hairs—several; gland-tipped; color—brownish.

I claim:

A new and distinct variety of rose plant of the hybrid tea class, substantially as herein shown and described, characterized particularly as to novelty by the unique combination of a vigorous habit of growth, an attractive general appearance of the foliage, a habit of bearing flowers usually singly to a stem, an unusually large flower size, and a distinctive and attractive Tyrian Purple general color tonality of the flowers.

No references cited.

ABRAHAM G. STONE, *Primary Examiner.*

R. E. BAGWILL, *Assistant Examiner.*